| United States Patent [19] | [11] | 4,112,102 |
|---|---|---|
| Thorpe | [45] | Sep. 5, 1978 |

[54] HALOPYRIDYL DERIVATIVES OF M-AMINOTETRAMISOLE AS ANTHELMINTICS

[75] Inventor: John E. Thorpe, Canterbury, England

[73] Assignee: Pfizer Inc., New York, N.Y.

[21] Appl. No.: 792,142

[22] Filed: Apr. 29, 1977

[30] Foreign Application Priority Data

May 1, 1976 [GB] United Kingdom ............... 17883/76

[51] Int. Cl.$^2$ .................... A61K 31/44; C07D 513/04
[52] U.S. Cl. ............................... 424/266; 260/294.8 C
[58] Field of Search .................... 260/294.8 C, 295 K, 260/295.5 B; 424/266

[56] References Cited

U.S. PATENT DOCUMENTS

| 3,274,209 | 9/1966 | Herman et al. .................... 260/306.7 |
| 3,673,205 | 6/1972 | Spicer et al. ...................... 260/306.7 |

FOREIGN PATENT DOCUMENTS 1,365,515  9/1974  United Kingdom ............. 260/294.8 C

*Primary Examiner*—Alan L. Rotman
*Attorney, Agent, or Firm*—Connolly and Hutz

[57] ABSTRACT

Novel derivatives of 6-(m-aminophenyl)-2,3,5,6-tetrahydroimidazo[2,1-b]thiazole(m-aminotetramisole) having anthelmintic properties are disclosed.

8 Claims, No Drawings

HALOPYRIDYL DERIVATIVES OF M-AMINOTETRAMISOLE AS ANTHELMINTICS

BACKGROUND OF THE INVENTION

This invention relates to novel derivatives of 6-(m-aminophenyl)-2,3,5,6-tetrahydroimidazo[2,1-b]thiazole (m-aminotetramisole) and to their use for controlling helminths in warm-blooded animals.

British patent specification No. 1,365,515 discloses 6-(mono, di- and tri-substituted phenyl)-2,3,5,6-tetrahydroimidazo[2,1-b] thiazoles useful in the treatment of gastrointestinal nematodes in warm-blooded animals.

U.S. Pat. No. 3,673,205 discloses dl or l-6-(m-aminophenyl)-2,3,5,6-tetrahydroimidazo[2,1-b]thiazole and their use as an anthelmintic.

U.S. Pat. No. 3,274,209 discloses dl-2,3,5,6-tetrahydro-6-phenyl-imidazo[2,1-b]thiazole and its use as an anthelmintic.

SUMMARY OF THE INVENTION

The present invention discloses the dl-(racemic) and l-forms of the compounds of the formula:

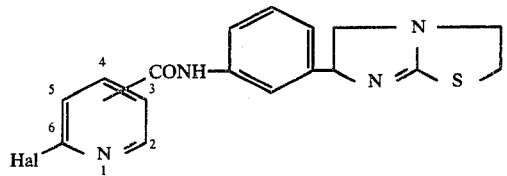
(I)

and the pharmaceutically acceptable acid addition salts thereof;
wherein Hal is F, Cl, Br or I and the —CONH group is attached to the 3-or 4-position of the pyridine ring.

Also disclosed is an anthelmintic composition useful for the treatment of helminth infections comprising a compound of formula (I) together with a pharmaceutically acceptable diluent or carrier.

In addition there is disclosed a method of treating helminth infectins in an infected host comprising administering to said host an anthelmintic amount of a compound of formula (I).

Further disclosed is a veterinary composition comprising an anthelmintic concentration of a compound of formula (I) in an animal feed.

"Hal" is preferably Cl, Br or I.

Typical non-toxic acid addition salts include the hydrochloride, hydrobromide, hydroiodide, nitrate, sulfate, acetate, lactate and citrate salts. The hydrochlorides are the preferred salts.

The compounds of the formula (I) in which the —CONH group is attached to the 3-position of the pyridine ring are preferred.

The preferred individual compounds are 6-[m-(6-chloronicotinoyl-amino)phenyl]-2,3,5,6-tetrahydroimidazo[2,1-b] thiazole (dl- or l-form), and the hydrochloride salts thereof.

The l-forms are the most preferred forms of the compounds of the invention.

DETAILED DESCRIPTION OF THE INVENTION

The compounds may be prepared by a number of routes, including the following:

(1) The compounds may be prepared by reacting the dl- or l-form of 6-(m-aminophenyl-2,3,5,6-tetrahydroimidazo[2,1-b]thiazole (m-aminotetramisole) of the formula:

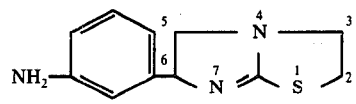
(II)

with an acid of the formula:

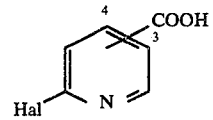
(III)

wherein the —COOH group is attached to the 3- or 4-position of the pyridine ring, or with its functional equivalent as an acylating agent, e.g. an acid halide, "activated" ester or mixed anhydride of the compounds of the formula (III).

The preferred acid halides are the acid chloride and bromide. They may be prepared by conventional procedures, e.g. by reacting the free acid with, respectively, thionyl chloride or bromide.

The preferred "activated" ester is the succinimido ester of the formula:

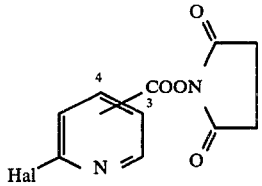
(IV)

wherein the —COO group is attached to the 3- or 4-position of the pyridine ring.

This may again be prepared by conventional procedures, e.g. by reacting the free acid with N-hydroxysuccinimide in the presence of a dehydrating agent e.g. dicyclohexylcarbodiimide. Another preferred "activated" ester is the phthalimido ester.

Suitable mixed anhydrides have the formula:

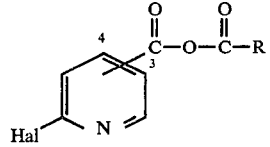
(V)

wherein the

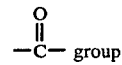

group is attached to the 3- or 4-position of the pyridine ring and wherein R is a $C_1$-$C_6$ alkyl or $C_1$-$C_6$ alkoxy group, preferably a t-butyl or iso-butoxy group. They may be prepared by conventional procedures, e.g. by reacting the free acid with the appropriate alkanoyl chloride or alkyl chloroformate, respectively, e.g. pivaloyl chloride or iso-butyl chloroformate, in the presence of a base such as triethylamine.

dl-(Racemic) or l-m-aminotetramisole should be used as the starting material according to whether the dl- or l-form, respectively, of the product (I) is required. dl-m-Aminotetramisole may be resolved into the d- and l-isomers by using the method described in U.S. Pat. Nos. 3,673,205 and 3,463,786. However, the l-forms of the product (I) may also be obtained by resolution of the dl-forms into its dextro and laevo antipodes. For this purpose, the procedure described in British Pat. No. 1,402,689 is possible.

Although the compounds of the invention may be prepared by reacting the compound (II) with the free acid (III), it is most preferred to use the acid in the form of its acid chloride or mixed anhydride (V) in which R is a $C_1$-$C_6$ alkyl group.

When the free acid form (III) is used, the reaction should generally be carried out in the presence of a dehydrating agent such as dicyclohexylcarbodiimide.

In a typical procedure involving the reaction of compound (II) with an acid chloride of compound (III), compound (II) is dissolved in a suitable solvent, e.g. aqueous methanol, the pH lowered to e.g. 5 with dilute hydrochloric acid, the mixture cooled, and the acid chloride added. After stirring the reaction mixture at room temperature for several hours, it may be diluted with a suitable solvent, e.g. methylene chloride, and the pH raised to e.g. 10 with a base such as sodium hydroxide. The organic layer is then separated, washed to neutrality with water, and the desired product may crystallize out on standing or may be recovered by evaporation of the solution to dryness.

In a typical procedure involving the reaction of compound (II) with a mixed anhydride of compound (III), compound (II) may be dissolved in a suitable solvent, e.g. aqueous methanol, the pH lowered to e.g. 5, the solution cooled, and the mixed anhydride added to the cooled solution. After stirring the reaction mixture at room temperature for several hours, a suitable solvent, e.g. methylene chloride, is added, and the pH raised to e.g. 10 by the addition of a base such as caustic soda.

The organic layer is separated, and washed with water which has been made slightly acidic (pH 6) with e.g. dilute hydrochloric acid. This extracts unreacted amine (II) into the aqueous phase. After separation, the organic phase is repeatedly washed with dilute aqueous hydrochloric acid (pH 1) to extract the product into an aqueous phase, impurities being retained in the organic phase, the aqueous washings being combined and basified to e.g. pH 10 with e.g. caustic soda. Fresh solvent, e.g. methylene chloride, is then added to extract the desired product into the organic phase. After separation and drying, the product may be obtained by evaporation of the organic phase to dryness. If necessary, the product may be re-crystallized from a suitable solvent, e.g. acetone.

(2) The compounds of the invention may also be prepared by cyclizing the dl (racemic)- or l-form of a compound of the formula:

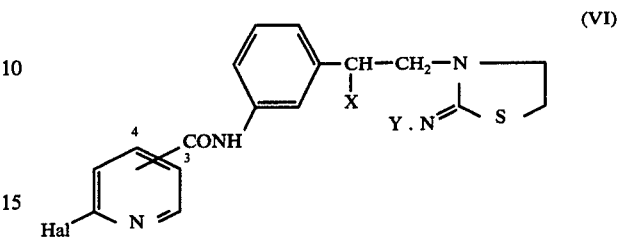

wherein the —CONH group is attached to the 3- or 4-position of the pyridine ring, Hal is as defined for formula (I), X is chlorine or bromine and Y is an imino-protecting group, preferably $C_1$-$C_4$ alkanoyl.

The preferred alkanoyl group is acetyl.

The cyclization of the compounds of the formula (VI) may be carried out in a manner analogous to the prior art, e.g. by heating them with excess of a base which does not hydrolyse the amide linkage, e.g. aqueous potassium carbonate, aqueous triethylamine, aqueous pyridine, or dilute ammonia solution. Typical conditions are 30°–100° C. for a few hours. Typically, chloroform is present in addition to the base, the chloroform layer being separated after reaction and evaporated to dryness to yield the desired product.

Generally the compounds of the formula (VI) are prepared by the reaction of the corresponding dl- or l-compounds in which X is OH or $C_1$-$C_4$ alkanoyloxy with a suitable halogenating agent, e.g. thionyl chloride or bromide. The l-forms of the corresponding compounds in which X is OH or $C_1$-$C_4$ alkanoyloxy may be prepared by resolution of the dl-form according to conventional procedures. If the dl-form of compound (VI) is used and the l-form of the final product is required then resolution may be carried out after the preparation of the latter. It is not essential to isolate the halogenated product (VI)—this may be cyclized in situ to the desired product by reaction with the base.

The compounds of the formula (VI) will often be obtained and cyclized in the form of their hydrochloride or hydrobromide salts.

The compounds of the formula (VI) may be prepared by methods analogous to the prior art, e.g. as follows:

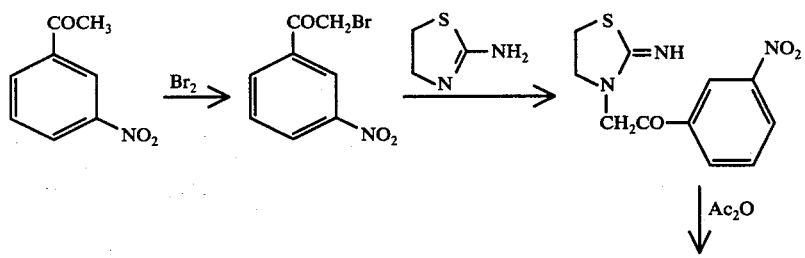

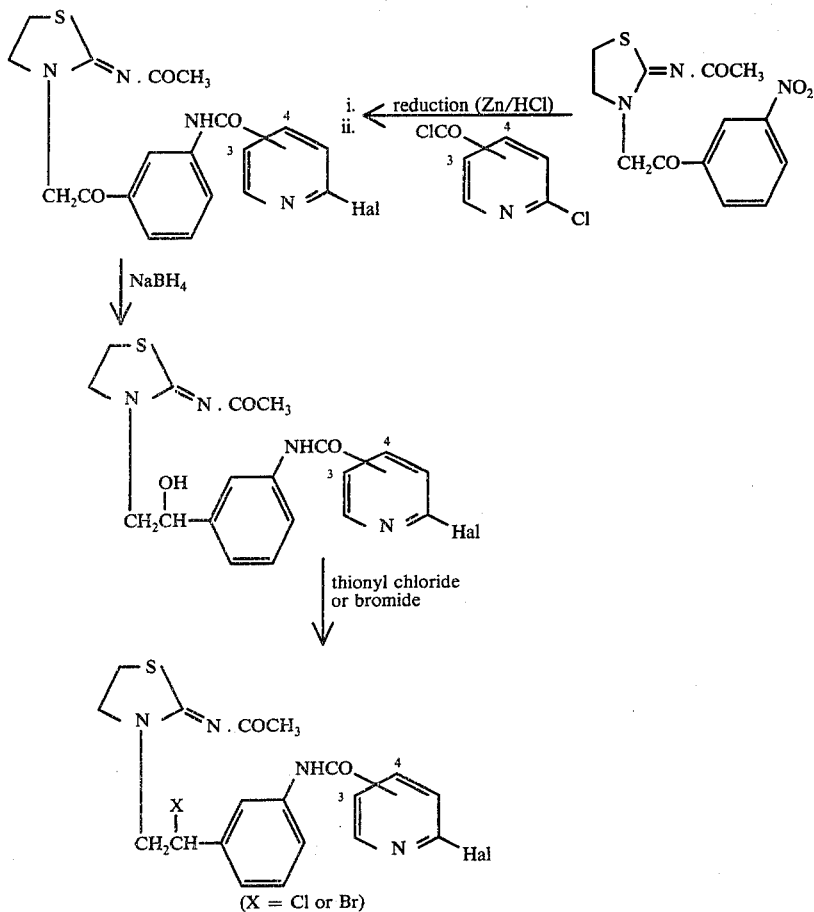

(Compounds of the formula (VI) in which Y is a $C_2$-$C_4$ alkanoyl or other imino-protecting group may be prepared in an analogous manner).

(3) The non-toxic acid addition salts of the invention may be prepared from the corresponding free base by conventional procedures. For example, the hydrochloride salts may be prepared by mixing a solution of the free base in a suitable solvent, e.g. ethanol, with a solution of hydrogen chloride in a suitable solvent, e.g. ethanol. The hydrochloride salt may generally be obtained as a precipitate on concentration of the resulting solution.

The compounds of the invention can be administered alone, but will generally be administered in admixture with a non-toxic diluent or carrier selected with regard to the intended route of administration. For example, they may be administered orally to animals as aqueous solutions or in admixture with an animal feedstuff or animal feed supplement. In parenteral administration, which is preferably carried out subcutaneously or intramuscularly, the carrier may be aqueous such as water or isotonic saline or non-aqueous such as polyethylene glycol. Parenteral administration of an aqueous solution is preferred, and such solutions will typically contain 1 to 10% by weight of the active compound. The compounds are also active when administered dermally, the active compound being adsorbed through the skin of the animal.

For human use the compounds may again be administered orally or parenterally, viz., as a tablet or capsule or by injection. The tablets or capsules or injectable formulations may again contain conventional diluents or carriers in addition to the active ingredient.

Suitable dose levels for human or animal use are from 1 to 50 mg. of the active ingredient per kg. of body weight.

Thus, for example, tablets or capsules may contain from 50 to 500 mg. of the active compound.

The compounds of the invention are particularly active against nematodes occurring in the stomachs and intestines of sheep and cattle.

Thus the invention provides an anthelmintic composition comprising a compound of the formula (I) as defined above, or a non-toxic acid addition salt thereof, and a non-toxic diluent or carrier.

The invention further provides a method of killing helminths in an infected animals, including a human being, which comprises administering to the animal an anthelmintic amount of a compound of the formula (I) as defined above, a non-toxic acid addition salt thereof or anthelmintic composition as defined above.

The following Examples, in which all temperatures are given in ° C, illustrate the invention.

EXAMPLE 1

A. 6-Chloronicotinoyl Chloride

6-Chloronicotinic acid (67 g) was treated with thionyl chloride (130 ml) and the resulting mixture heated under reflux for 2 hours. After evaporation to dryness, 60°-80° petroleum ether (60 ml) was added, and the solution again evaporated to dryness. The resulting residue was taken up in petroleum ether (60°-80°) and the solution filtered. Partial evaporation of the filtrate, followed by cooling, gave the desired product, 6-chloronicotinoyl chloride, as a white precipitate, m.p. 45°-47° (73). The product was characterized by infra-red spectroscopy, and was used directly in the next stage without further purification.

B.
dl-6-{m-(6-Chloronicotinoylamino)phenyl}-2,3,5,6-tetrahydroimidazo [2,1-b]thiazole

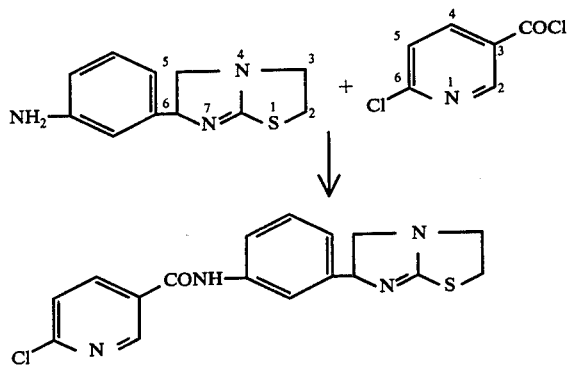

dl-6-(m-Aminophenyl)-2,3,5,6-tetrahydroimidazo[2,1-b]thiazole (dl-m-aminotetramisole) (42 g) was dissolved with stirring in aqueous methanol (200 ml methanol/50 ml water), and the pH was adjusted to 5 with 2N hydrochloric acid. The mixture was then cooled in an ice/water mixture and 6-chloronicotinoyl chloride (67 g—prepared as in Part A above) was added. The resulting mixture was stirred at room temperature overnight. The mixture was then diluted with methylene chloride (about 500 ml), and pH adjusted to 10 with 1N sodium hydroxide. The organic layer was separated, washed to neutrality with water, and allowed to stand, when the desired product, dl-6-(m-(6-chloronicotinoylamono)phenyl)-2,3,,5,6-tetrahydroimidazo[2,1-b]thiazole (52.6 g), m.p. 135°-138°, crystallied out. The product was filtered off. Evaporation of the filtrate produced a second crop (6.8 g) of the product.

Analysis %: Found: C, 54.75; H, 4.18; N, 15.04. Calculated for $C_{17}H_{15}ClN_4OS.1/2H_2O$: C, 55.51; H, 4.35; N, 15.24.

C. Monohydrochloride salt of dl-6-(m-(6-chloronicotinoylamino)phenyl)2,3,5,6-tetrahydroimidazo[2,1-b]thiazole The product of Part B (58.4 g) was partially dissolved in ethanol (800 ml) by warming. Hydrogen chloride gas (6 g.) in ethanol (300 ml) was then added and a complete solution was obtained. Evaporation of the mixture to a smaller volume yielded crystals which were found by N.M.R. analysis ($DMSOd_6$) to contain 1 mole of ethanol. To remove the ethanol to crystals were dried in a vacuum oven at 90° for 3 days, yielding the desired product, the monohydrochloride salt of dl-6-(m-(6-chloronicotinoylamino)phenyl)-2,3,5,6-tetrahydroimidazo[2,1-b]thiazole (52.3 g), m.p. 230°-235°.

Analysis %: Found: C, 50.35; H, 4.16; N, 13.40; Cl, 8.51. Calculated for $C_{17}H_{15}N_4ClOS.HCl.1/2H_2O$: C, 50.50; H, 3.96; N, 13.86; Cl, 8.79.

EXAMPLES 2 TO 5

The following dl-imidazo[2,1-b]thiazole derivatives were prepared by procedures similar to those of Example 1, starting from the appropriate halopyridine carboxylic acid and thionyl chloride:

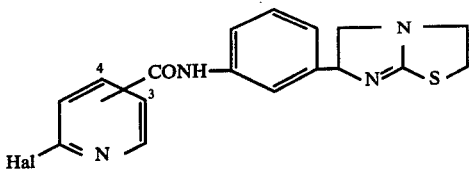

| Ex. No. | Hal | Position of attachment of —CONH to pyridine nucleus | Form isolated | m.p. (°C) | Analysis % (Theoretical in brackets) | | |
|---|---|---|---|---|---|---|---|
| | | | | | C | H | N |
| 2 | chloro | 4-position | free base, ½ H₂O | 188–189° | 56.22 (56.19 | 4.03 4.27 | 15.05 14.43) |
| 3 | chloro | 4-position | mono-hydrochloride, ½ H₂O | 248–9° | 50.90 (50.50 | 4.09 3.96 | 13.96 13.86) |
| 4 | fluoro | 3-position | free base, 2 H₂O | 115–120° | 53.85 (53.96 Molecular weight from mass spectral data 342 | 4.33 5.02 | 13.88 14.80) |
| 5 | fluoro | 4-position | free base, 1 H₂O | 158–9° | 56.49 (56.66 | 4.28 4.72 | 15.43 15.55) |

EXAMPLE 6

A. 6-Bromonicotinic Acid

Phosphorus pentabromide (18 g.) was added carefully to 6-hydroxynicotinic acid (4.17 g) and the resulting mixture was heated with stirring for about ¼ hour at 70°-80° and then 1 hour at 120°. During the heating, the resulting dark red liquid solidified to a yellow mass. After cooling, the mass was added to iced water, and the resulting white precipitate of 6-bromonicotinic acid was filtered off, washed with water, and recrystallized from aqueous ethanol (yield 4g, m.p. 190°-195°). The compound was used directly in the next stage.

B. 6-Bromonicotinic Acid, Anhydride with Pivalic Acid

6-Bromonicotinic acid (2.02 g, prepared as in Part A above) was stirred in dry ether (50 ml) containing triethylamine (1 g). Pivaloyl chloride (1.2 g) was dissolved in dry ether (10 ml) and added dropwise over a period of 15 minutes to the solution of the nicotinic acid, which was stirred and maintained at 0°. The resulting white suspension was stirred at 0° for a further ½ hour, and then at room temperature for 1½ hours. The precipitate of triethylamine hydrochloride was filtered off. The filtrate was washed with dilute aqueous sodium bicarbonate and then water, dried over anhydrous magnesium sulphate, and evaporated to yield the desired product, the anhydride of 6-bromonicotinic acid with pivalic acid, as a white solid (2.8 g). The anhydride was characterized by Infra-Red Spectroscopy and was used in the next stage without further purification.

C.

dl-6-{m-(6-bromonicotinoylamino)phenyl}-2,3,5,6-tetrahydroimidazo[2,1-b]thiazole

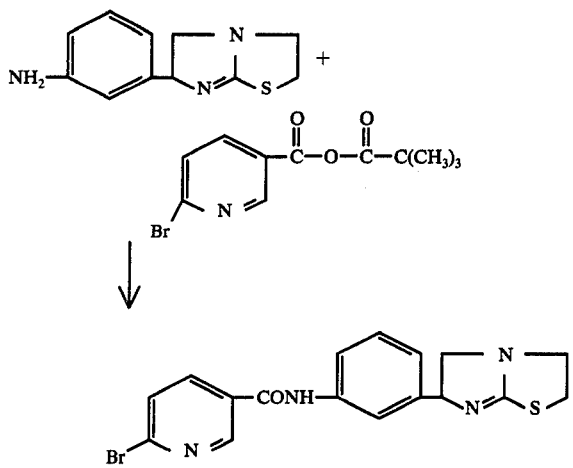

The anhydride prepared in Part B (1.76 g) was added to a solution of dl-6-(m-aminophenyl)-2,3,5,6-tetrahydroimidazo[2,1-b]thiazole (880 mg) in cold (0°–10°) aqueous methanol (16 ml methanol/4 ml H$_2$O); the pH of the methanol solution having been adjusted to 5 with dilute hydrochloric acid prior to the addition of the anhydride. The resulting mixture was stirred at room temperature for 24 hours. Methylene chloride (50 ml) and water (5 ml) were then added and the pH was adjusted to 10 with 2N sodium hydroxide. The organic layer was separate, washed with water at pH 6 containing dilute hydrochloric acid to extract unreacted amine into the aqueous phase, separated, and repeatedly washed with dilute aqueous hydrochloric acid at pH 1 to remove further impurities. The aqueous phases from the repeated washings with the pH 1 hydrochloric acid were combined, basified with 2N sodium hydroxide to pH 10, and extracted with methylene chloride. After separation, the organic phase was dried, and the solvent removed by evaporation to yield a white solid, dl-6-(m-(6-bromonicotinoylamino)phenyl9-2,3,5,6-tetrahydroimidazo[2,1-b]thiazole, which was recrystallized from acetone. The yield of the product was 204 mg, melting at 149°–153°, molecular weight from mass spectral data 403.

Analysis %: Found: C, 50.96; H, 4.30; N, 12.81. Calculated for C$_{17}$H$_{15}$N$_4$OSBr: C, 50.62; H, 3.72; N, 13.89.

EXAMPLES 7–9

The following dl-imidazo[2,1-b]thiazole derivaives were prepared by procedures similar to those of Example 6, Part C, starting from dl-6-(m-aminophenyl)-2,3,5,6-tetrahydroimidazo[2,1-b]thiazole and the anhydride of the appropriate halopyridinecarboxylic acid with pivalic acid:

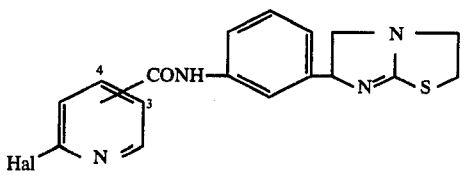

| Ex. No. | Hal | Position of attachment of —CONH to pyridine nucleus | Form Isolated | m.p. (° C) | Analysis % (Theoretical in brackets) | | |
|---|---|---|---|---|---|---|---|
| | | | | | C | H | N |
| 7 | I | 3-position | Free Base | 200–205 | 45.72 (45.33 | 3.58 3.73 | 12.28 12.44) |
| 8 | Br | 4-position | Free Base | 190–191 | 50.67 (50.62 | 3.70 3.72 | 13.92 13.90) |
| 9 | I | 4-position | Free Base, 1 H$_2$O | 202–204 | 44.37 (43.58 | 3.48 3.63 | 12.16 11.96) |

EXAMPLE 10

A.

1-6-(m-(6-Chloronicotinoylamino)phenyl)-2,3,5,6-tetrahydroimidazo[2,1-b]thiazole 1-m-Aminotetramisole (3.0 g) was dissolved in a methanol (40 ml)/water (10 ml) mixture and brought to pH 5 with dilute hydrochloric acid. The resulting mixture was stirred at 0° and 6-chloronicotinoyl chloride (4.8 g) was then added. The mixture was stirred at room temperature (25°) overnight, made alkaline with 2N sodium hydroxide, and separated. The aqueous layer was extracted with methylene chloride. The organic layers were combined and washed to neutrality with small amounts of dilute hydrochloric acid. The organic solution was then evaporated to a smaller volume until the desired product (3.9 g) crystallized. The product, which was characterized by thin layer chromatographic analysis, had an R$_f$ identical to that of the product of Example 1.

B. Hydrochloride of L-6-(m-(6-chloronicotinoylamino)phenyl)-2,3,5,6-tetrahydroimidazo[2,1-b]thiazole The free base prepared in Part A (3.9 g) was partially dissolved in hot ethanol and a slight excess of ethanolic hydrogen chloride was then added to give a complete solution, which was evaporated to dryness. Ether and a small amount of ethanol were then added, and the resulting mixture stirred overnight. Theprecipitated hydrochloride salt was then filtered off, washed with ether, and dried. The yield of the product was 4.3 g, m.p. 220°–225° (d), $[\alpha]_{589}^{25} = 110.6°$ (c = 0.5 g/100 ml methanol).

Analysis %: Found: C, 51.49; H, 4.01; N, 14.27; Cl$\ominus$ 8.85. Calculated for C$_{17}$H$_{15}$N$_4$ClOS.HCl C, 51.65; H, 4.05; N, 14.18; Cl$\ominus$ 8.99.

The activity of the compounds in a triple infection mouse screen against a concurrent infection of *Nematospiroides dubius*, *Syphacia obvelata* and *Hymenolepsis nana* may be determined as follows. Albino mice, 20 grams in weight, are infected and treated according to the following procedure. Taking the initial infection as day 0, mice are infected with 2,000 *H. nana* ova on day 0 and 100 *N. dubius* larvae on day 5 and then exposed to a Syphacia infected colony for 4 days. The mice are then treated with test compound in groups four either once on day 14 or on three consecutive days 14–16 by the oral or subcutaneous route. The mice are autopsied on day 19 and examined for the presence of worms. The results obtained are compared with those from an untreated infected control (12 per group). For *N. dubius* total counts are carried out and activity is expressed as a percentage reduction. Infections of the other parasites are graded, Syphacia (0–3) and *H. nana* (0–3) and activity is expressed by comparing group mean grades. Polyethylene glycol is the standard vehicle used in the preparation of the test compounds for dosing, although aqueous solutions are used for water-soluble substances, and materials insoluble in both polyethylene glycol and water may be ball-milled in aqueous 1% Tween 80. The mg/kg. levels used may be for example up to 12.5 mg/kg.

The activities of the compounds of the invention against the helminth *N. dubius* using the above method was found to be as follows:

|  |  | Dose (mg/kg) | | |
|---|---|---|---|---|
| Compound |  | 12.5 | 6.2 | 3.1 |
| Product of Example 1 Part B | % clearance | 100 | 100 | 97 |
| Product of Example 1 Part C | % clearance | 100 | 100 | 100 |
| Product of Example 2 | % clearance | 100 | 96 | 94 |
| Product of Example 3 | % clearance | 98 | 99 | 62 |
| Product of Example 4 | % clearance | 74 | 85 | 62 |
| Product of Example 5 | % clearance | 89 | 84 | 58 |
| Product of Example 6 | % clearance | 99 | 98 | 89 |
| Product of Example 7 | % clearance | 98 | 91 | 80 |
| Product of Example 8 | % clearance | 99 | 99 | 76 |
| Product of Example 9 | % clearance | 100 | 75 | 55 |
| Product of Example 10 Part A | % clearance | 100 | 100 | 100 |

EXAMPLE 11

The following Examples illustrate compositions according to the invention:

An aqueous composition suitable for administration by injection to human or non-human animals is as follows:

| Monohydrochloride salt of dl | 6-{m-6(-chlor- nicotinoylamino- phenyl}2,3,5,6- tetrahydroimi- dazo[2,1-b thia- zole] | up to 10% w/v |
|---|---|---|
| Methadioxole or PEG 300 | — | up to 50% w/v |
| water | — | balance to 100% |

The composition may be prepared by mixing the ingredients together, and may be administered in one or more doses.

Obviously the amount of the active ingredient will vary according to the dose response and weight of the animal but will generally be in the range of 1 to 50 mg per kg. of body weight, typically 12.5 mg/kg.

EXAMPLE 12

Administration of the compounds of the invention to animals may conveniently be carried out by incorporating them into feed mixtures. The typical dose used will be 1 to 50 mg/kg of body weight per day, i.e. 500 to 25 gm per day for 500 kg. cattle. Assuming such an animal consumes 5 kg. of feed supplement per day, then the said quantity of the active material may be mixed with 5 kg. of feed supplement.

What is claimed is:

1. The dl- and l-forms of the compounds of the formula:

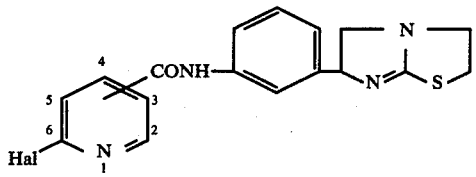

and the pharamceutically acceptable acid addition salts thereof,
wherein Hal is F, Cl, Br or I and the —CONH group is attached to the 3- or 4-position of the pyridine ring.

2. A compound as claimed in claim 1 wherein the —CONH group is attached to the 3-position of the pyridine ring.

3. A compound as claimed in claim 1 wherein the compound is in the form of a hydrochloride, hydrobromide, hydroiodide, nitrate, sulfate, acetate, lactate or citrate salt.

4. l- or dl-6-[m-(6-chloronicotinoylamino)phenyl]-2,3,5,6-tetrahydroimidazo [2,1-b] thiazole, and the hydrochloride salts thereof.

5. An anthelmintic composition useful for the treatment of helminth infections comprising an anthelmintic effective amount of a compound as claimed in claim 1 together with a pharmaceutically acceptable diluent or carrier.

6. A method of treating helminth infections in an infected host comprising administering to said host an anthelmintic effective amount of a compound as claimed in claim 1.

7. A method as claimed in claim 6 comprising administering from about 1 to 50 mg per kg of body weight daily of said compound.

8. A veterinary composition comprising an anthelmintic concentration of a compound as claimed in claim 1 in an animal feed.

* * * * *